(12) United States Patent
Schlögl et al.

(10) Patent No.: US 6,653,509 B2
(45) Date of Patent: Nov. 25, 2003

(54) METHOD FOR THE LIQUID-PHASE HYDROGENATION OF ORGANIC MATERIALS

(75) Inventors: Robert Schlögl, Berlin (DE); Michael Wohlers, Eschborn (DE); Thilo Belz, Berlin (DE); Thomas Braun, Berlin (DE)

(73) Assignee: Max-Planck-Gesellschaft zur Förderung der Wissenschaften e.V., München (DE)

( * ) Notice: Subject to any disclaimer, the term of this patent is extended or adjusted under 35 U.S.C. 154(b) by 22 days.

(21) Appl. No.: 10/121,728

(22) Filed: Apr. 15, 2002

(65) Prior Publication Data

US 2002/0132863 A1 Sep. 19, 2002

Related U.S. Application Data

(60) Division of application No. 09/535,748, filed on Mar. 27, 2000, now abandoned, which is a continuation-in-part of application No. 09/147,760, filed as application No. PCT/EP97/04842 on Sep. 5, 1997, now abandoned.

(30) Foreign Application Priority Data

Sep. 6, 1996 (DE) .......................................... 196 36 269

(51) Int. Cl.⁷ ..................... C07C 209/00; C07C 37/00; C07C 27/00; C07C 5/00
(52) U.S. Cl. ..................... 564/416; 568/772; 568/814; 568/862; 585/250; 585/260
(58) Field of Search .......................... 564/416; 568/772, 568/814, 862; 585/250, 260

(56) References Cited

U.S. PATENT DOCUMENTS

| 4,116,996 A | 9/1978 | Huang |
| 4,324,695 A | 4/1982 | Hinnenkamp |
| 4,569,924 A | 2/1986 | Ozin |
| 5,227,038 A | 7/1993 | Smalley et al. ............. 423/446 |

FOREIGN PATENT DOCUMENTS

| EP | 43 24 693 | 2/1995 |
| GB | 2 217 701 | 11/1989 |
| WO | WO 95/10481 | 4/1995 |

OTHER PUBLICATIONS

Harris, *International Materials Review*, 1997, vol. 42, No. 5, "Structure of Non–Graphitising Carbons".

Tsang, et al., "Reduction of Nitric Oxide by Arc–Vaporized Carbon", *Applied Catalysis B.*, vol. 8, pp. 445–455, Jul. 1996.

Belz, et al., "Characterization of Fullerene Soots and . . . Electrode Deposits", *Synthetic Metals*, vol. 77, pp. 223–226, 1996.

*Primary Examiner*—James O. Wilson
*Assistant Examiner*—Sikarl A. Witherspoon
(74) *Attorney, Agent, or Firm*—Rothwell, Figg, Ernst & Manbeck, P.C.

(57) ABSTRACT

A catalyst which consists of amorphous carbon with molecular planes that have curved surfaces and contain six-membered and non-six-membered carbon rings, optionally having at least one catalytically active, low-valency metal covalently bound thereto. Methods of producing the catalyst and applications thereof are included.

4 Claims, 3 Drawing Sheets

METHOD FOR THE LIQUID-PHASE HYDROGENATION OF ORGANIC MATERIALS

This is a Division of application Ser. No. 09/535,748 filed Mar. 27, 2000, which is a CIP of application Ser. No. 09/147,760 filed May 4, 1999, which is a 371 of PCT/EP97/04842 filed Sep. 5, 1997. The disclosure of the prior applications is hereby incorporated by reference herein in its entirety.

FIELD OF THE INVENTION

The invention relates to a catalyst which consists of amorphous carbon with molecular planes that have curved surfaces and contain six-membered and non-six-membered carbon rings, optionally having at least one catalytically active, low-valency metal covalently bound thereto. The invention also relates to methods of producing the catalyst and applications thereof.

In many applications involving the use of catalytically active metals on a support system, it is of advantage if the latter is a carbon-based system. However, the use of graphitic material as support has the disadvantage that, due to the graphite's planar layering, there is only little interaction with the metals. As a result, the metal is apt to agglomerate, especially under reaction conditions and in particular at elevated temperatures. Agglomeration of the catalytically active metal means that the surface area thereof is reduced, which in turn causes a reduction in the catalytic activity of the system and thus, especially in the case of valuable metals, inadequate exploitation of the system's catalytic capacity.

In patent specification DE 43 24 693.1, the inventor has already suggested over-coming this disadvantage by using metal-fullerene intercalation compounds. These have the advantage of being defined compounds which are not only highly stable on account of their bonding strongly to the catalytically active metals, but can also be reproduced exactly. This is largely due to the fact that direct covalent bonds are formed between the carbon atoms of the fullerene molecule and a metal atom.

One disadvantage of using metal-fullerene intercalation compounds as catalysts is the fact that the supporting material is expensive. In addition, it would be beneficial if the catalytic efficacy—expressed in terms of the content of catalytically active metal or metal compound used in each case—could be enhanced further by making the metal more accessible for the components of the catalysed reaction. The object of this invention is thus to overcome the above-mentioned disadvantages of catalysts with a carbon-based support.

SUMMARY OF THE INVENTION

This object is achieved by means of a catalyst which consists of amorphous carbon with molecular planes that have curved surfaces and contain six-membered and non-six-membered carbon rings, optionally having at least one catalytically active, low-valency metal covalently bound thereto.

The invention is based on the surprising discovery that amorphous, carbon with molecular planes exhibiting curved surfaces and containing not only six-membered but also non-six-membered carbon rings are suitable as catalysts and/or as supporting material for catalytically active metals, and have especially desirable properties that result in superior catalysts. Without being bound by theory, it is assumed that this is due to the presence of curved $sp^2$-hybridized carbon layers. The curvature of the layers is not due in this case to simple "rolling" or "bending" of otherwise intact graphite layers, but is due to the incorporation of non-six-membered rings in the $sp^2$-hybridized carbon layers. The curvature produced thus in the carbon layers is associated with significant differences compared to the geometric and electronic structure of a planar, graphitic $sp^2$-hybridized carbon layer. Besides a considerable stress-induced increase in potential energy, the $\pi$ electrons are not completely delocalized within these curved areas, so that the curved carbon layers can be seen to a certain extent as conjugated double-bond systems.

Thus, the presence of non-six-membered rings in the carbon network not only introduces curvature into the surface of the materials described, but also a modulation of its electronic structure. The combined action of these two effects gives rise to the presence of anchoring sites for metal particles as well as of catalytically active sites.

When used as supporting materials for catalytically active low-valency metals, the carbon material used in the catalysts of the invention, like electron-deficient olefins, are able to form chemical bonds with transition metals in low formal oxidation states. These bonds are chemical bonds formed directly between the metal and the carbon support. They do not, as is the case with conventional carbon supports such as activated charcoal, anchor the metal atoms primarily by way of interactions with terminal heteroatom functionalities, predominantly oxygen.

The amorphous carbon contained in the catalysts of the invention consists of interlacing 6-C rings in which additional rings, mainly 5-C rings, are incorporated. The curved surfaces may be concave or convex. This structure, which is an essential feature of the amorphous carbon used in the catalyst of the invention, can be determined by physical methods, especially x-ray absorption spectroscopy (XAS), as is described by H. Werner et al., in Chem. Phys. Letters 194 (1992), 62–66. The curved areas can also be characterized by their special chemical reactivity; corresponding reaction products have been characterized by IR spectroscopy after partial oxidation of these carbon materials (M. Wohlers, A. Bauer, R. Schlögl, Microchim. Acta, submitted 1995, printing). An example of the materials suitable in the context of the invention is the product known as "Krätschmer soot". This is a product which, during the production of fullerenes by the Krätschmer method, is left behind when the fullerenes are separated off. As described in more detail below, the amorphous carbon of the catalyst of the invention may also be obtained by methods other than the one described by Krätschmer.

BRIEF DESCRIPTION OF THE DRAWINGS

FIG. 2 thus demonstrates that the catalysts of the invention boast better thermal stability under reaction conditions.

DESCRIPTION OF THE PREFERRED EMBODIMENTS

Figure 1:
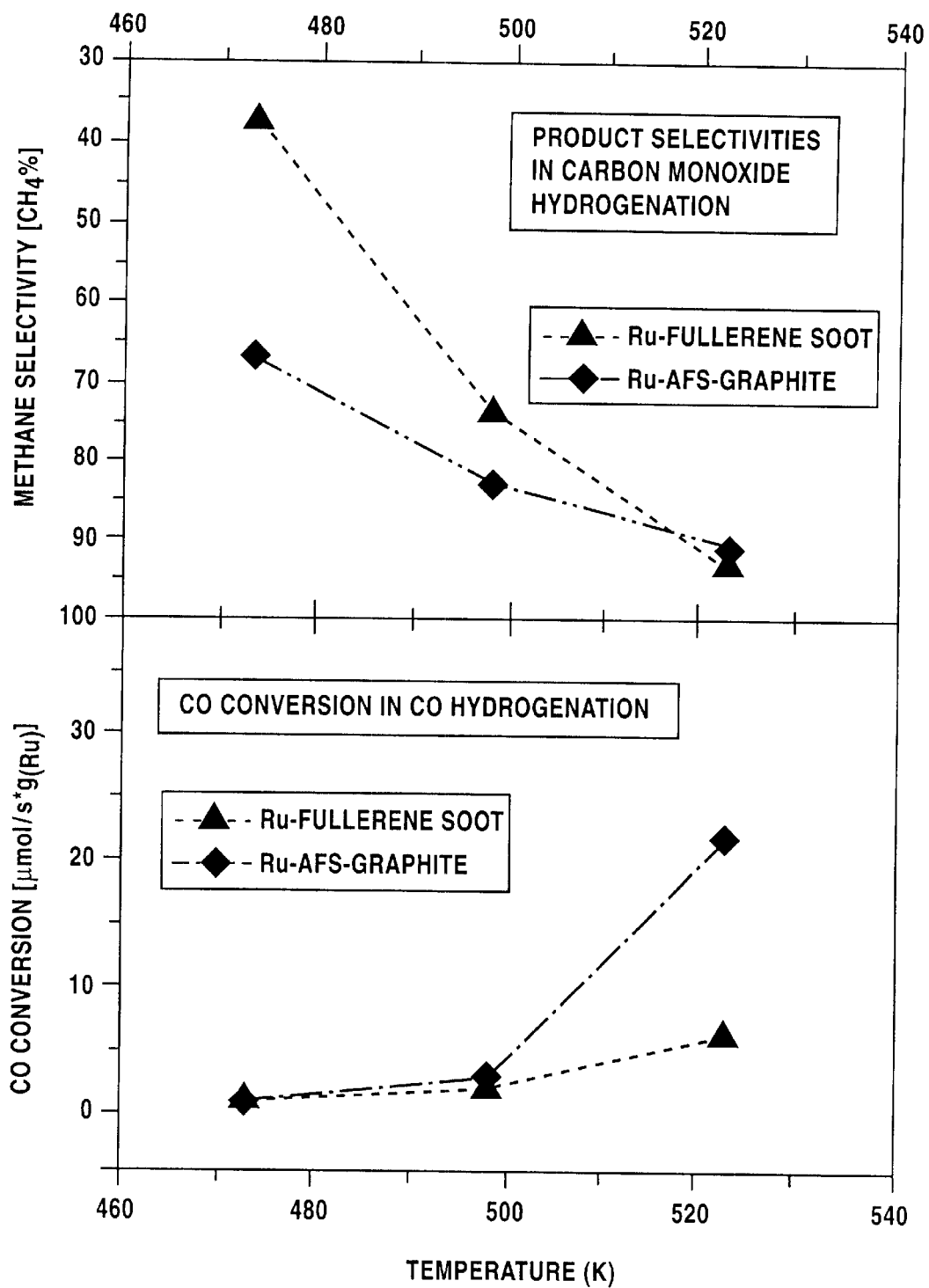
FIG. 1 shows CO conversion and product selectivity with a ruthenium-containing catalyst according to the invention and with ruthenium-AFS-graphite. In the lower half of FIG. 1, the gas-chromatographically determined amount of CO converted in the presence of each of the catalysts is compared at different temperatures. CO conversion is a measure of the catalytic activity of the heterogeneous systems. In the upper half of FIG. 1, the methane selectivity of the two systems is compared. The methane selectivity is given by the percentage of methane in the resulting hydrocarbon mixture, which contains, among other compounds, ethane, ethene and other aliphatics, right up to octane. This part of FIG. 1 shows clearly that at low temperatures, the catalyst of the invention produces a greater proportion of hydrocarbons with a higher molecular weight than the corresponding ruthenium-graphite catalyst does.

Metal particles containing 10 to 1000 atoms are able to form the covalent bonds characteristic of the catalysts of the invention. With larger metal particles, the strength of the bonds decreases. As the size of the metal particles increases, the binding strength finally decreases to a value which, for the size of the metal particles, is no longer significantly greater than the binding strengths of conventional carbon supports.

The amorphous carbon contained in the catalysts of the invention differ from fullerenes in that the reactive double bonds in the curved carbon layers are an integral component of the amorphous carbon of the invention, whereas fullerenes consist of defined, individual molecules. Among the amorphous carbon materials which are suitable for the catalysts of the invention, for example, are fullerene soot residue and the product known as "onion carbon". It has onion-like structures with a diameter of 100 Å or more, which are embedded firmly in the surrounding carbon. Fullerenes, by contrast, have a diameter of about 10 Å, and are molecular.

Besides the aforementioned Krätschmer method, with subsequent separation of the fullerenes, there are other methods of producing the amorphous carbon materials contained in the catalyst of the invention. These include, in particular, the high frequency vaporization of graphite, laser vaporization of graphite, and the pyrolysis of hydrocarbons under suitable conditions. A preferred method of obtaining the amorphous carbon is to vaporize pure graphite in an enclosed apparatus containing at least two electrodes and having an inert atmosphere to produce a vaporized composition containing fullerene soot residue and which may also contain more-or-less fully-formed fullerenes, rapidly cool the vapor to deposit the composition on a surface of the apparatus and/or the electrodes and then remove any fullerenes contained in the composition by way of solvent extraction.

The superior catalytic properties of the metal-containing catalysts described in the invention are attributed to the fact that all the catalytically active metal is anchored at the surface and therefore very readily accessible for the components of the reaction being catalysed. In the case of the transition metal/fullerene compounds, by contrast, a significant proportion of the catalytically active metal is in the interior of the macroscopic particles of transition metal/fullerene compound, and therefore inaccessible for the components of the reaction being catalysed. The superior stability of the metal-containing catalysts of the invention compared to graphite-based catalysts is attributed to the covalent bonds formed with the metal.

Low-valency metals are understood in the context of this invention to mean metals in the avalent, monovalent and divalent states. Preference is given to metals in the avalent state, with the familiar stabilizing ligands such as carbonyls, isonitriles, phosphines, phosphites, alkenes, polyalkenes, heteroalkenes, alkines and cyclically conjugated systems such as benzene or cyclopentadienyl anions. Examples of suitable avalent, catalytically active metal complexes include triruthenium dodecacarbonyl, platinum dibenzylidene acetone, palladium dibenzylidene acetone, palladium tetrakistriethyl phosphine, nickel tetracarbonyl, iron pentacarbonyl, nonacarbonyldiiron, dodecacarbonyltriiron and so on. Some of these compounds are commercially available, while others can be prepared using standard methods, such as are described in the Handbuch der präparativen anorganischen Chemie, vol. 3, publishing house F. Encke in Stuttgart, Germany. Suitable mono- or divalent compounds include such compounds as can be reduced to the avalent state under reaction conditions, if necessary by adding a reagent that acts as reducing agent, for example, molecular hydrogen, carbon monoxide or sodium borohydride. Suitable catalytically active metals are preferably metals from groups Ib, VIIb or VIIIb of the periodic table, rare-earth metals that form low-valency compounds, or titanium or vanadium. Special preference is given to platinum, ruthenium, palladium and iron.

Other suitable metals include, eg, nickel, cobalt, manganese, osmium, iridium and rhenium, and also titanium and vanadium provided they can be reduced to the low valency state.

A particularly interesting aspect of the invention is the qualitative change which can be achieved in the catalytic properties of the bound metal. It was possible to demonstrate that the structural properties of the metal particles contained in the systems described in the invention differed markedly from those of the metals in comparable metal/graphite systems. These structural differences are attributed to qualitatively different attractive interactions between the metal particles and the carbon support system in question. The structural differences in the metal particles are not, however, exclusively of geometrical nature; it is assumed that there are also differences in the electronic structure, as a result of which the active centers at the surface of the metal, which are crucial for the heterogeneous catalysis of a reaction, exhibit different properties. For example, when the catalysts of the invention are used in the hydrogenation of carbon monoxide, one achieves a shift in selectivity to products of higher molecular weight, these being the products primarily sought after in this process.

Compared to catalysts with graphite as supporting material, the catalysts of the invention have the general advantage of retaining their stability at elevated temperatures. Besides this, they are often quantitatively superior under otherwise comparable conditions, and in other cases also exhibit qualitatively different catalytic properties.

An additional subject of the invention is a method of producing the new catalysts. According to the method of the invention, graphite is vaporized in a non-oxidizing atmosphere by means of an electric arc struck between at least two graphite electrodes in a vacuum apparatus, during which process one a) works with a.c. or d.c. under a pressure of 100 Pa or less in a vacuum apparatus the walls of which are cooled, the product being deposited on the cooled walls, or b) works with d.c. under a pressure of 1 to 100 kPa and arc lengths of 0.1 to 20 mm, the product accumulating on the electrode connected to the negative pole of the power supply, or c) with a.c. under a pressure of 1 to 100 Pa and arc lengths of 0.1 to 20 mm, the product accumulating on the carbon electrodes.

Optionally, according to one embodiment of the present invention, thereafter the product of a), b) or c) may be reacted with a thermolabile, low-valency compound or complex of a catalytically active metal.

The graphite used should be as pure as possible. It is preferable to work in a noble-gas atmosphere, most preferably of helium, argon or a mixture of helium and argon. Use can also be made, e.g., of hydrogen, nitrogen or ammonia.

If the amorphous carbon is produced according to procedure a), it is expedient to cool the walls of the vacuum apparatus with water. However, other cooling methods or coolants can be used in a similar manner. For preparing the amorphous carbon it is also of advantage to work with two graphite electrodes, since this is how a commercially available apparatus is usually equipped. However, for the method of the invention it is also possible to use modified electric-arc equipment with more than two graphite electrodes.

As mentioned earlier, the amorphous carbon may also be one prepared according to the method of Krätschmer (W. Krätschmer et al., Chemical Physics Letters, vol. 170 (1990), p. 167–170), which has been freed from fully-formed fullerenes by extraction thereof.

The reaction of the amorphous carbon with the metal compound is preferably performed in the absence of air in a suspension of the supporting carbon in a solvent in which the metal compound is soluble. It is of advantage to work at an elevated temperature, preferably at the reflux temperature of the solvent. Under these conditions, the reaction is generally allowed to proceed for between 1 and 50 hours, preferably between 15 and 30 hours. If the support material contains fullerenes, these are removed prior to the reaction, preferably by extraction with a suitable organic solvent.

The general temperature range for the reaction of the amorphous carbon with the metal is between the solidification point of the solvent and its boiling point. The boiling point of the solvent can be raised according to standard practice by applying pressure; pressures up to 100 MPa, preferably up to about 10 MPa, may be used.

Suitable solvents include aromatics, halogenated aromatics, organo-chlorinated compounds and heterocyclics such as benzene, toluene, xylene, ethylbenzene, chlorobenzene, dichlorobenzene, carbon tetrachloride, chloroform, dichloromethane and tetrahydrofuran.

The catalysts of the invention are generally suitable for reactions which proceed under transition-metal catalysis. The hydrogenation of carbon monoxide is a preferred application. Other reactions for which the catalysts of the invention are especially suitable are, e.g., liquid-phase hydrogenations of organic molecules, these being conducted preferably at a temperature between the solidification point of the compound to be hydrogenated or of the solvent used and 150° C.

Furthermore, the catalysts of the invention are especially suitable for partial oxidation reactions of organic molecules.

Using the catalysts of the invention, the reaction can be carried out either in the liquid phase or by passing a gaseous mixture of the reagents over the catalyst, e.g., in a fixed-bed reactor. Partial oxidations of this kind are suitable, e.g., for the oxidation of alcohols, aldehydes, alkanes and the dehydrogenation of hydrocarbons.

Liquid-phase hydrogenations of this kind are suitable, e.g., for the hydrogenation of olefins, ketones, aromatic nitro compounds and substances of comparable reactivity. These hydrogenations can be conducted directly with the substance in question (provided the compound to be reduced is liquid under the conditions of the hydrogenation reaction) or with the substance in solution. Suitable solvents in the latter case include tetrahydrofuran, dichloromethane and toluene.

The following examples serve, together with the drawings, to explain the invention in more detail.

EXAMPLES

1a. Production of the Ruthenium Catalyst (1) In a helium atmosphere and under a pressure of 100 Pa, graphite was vaporized in an electric arc struck between two a.c.-operated graphite electrodes in a water-cooled vacuum apparatus. The desired product was deposited on the water cooled walls of the apparatus. After vaporization had been concluded and the apparatus had cooled, the product was collected and suspended in toluene. Triruthenium dodecacarbonyl $Ru_3(CO)_{12}$ was added to this suspension at room temperature and dissolved therein. The suspension was then brought slowly to the boil, and refluxed for one day. The insoluble catalyst was then separated from the solvent, washed with solvent and dried at room temperature under vacuum. The catalyst obtained was not subjected to any additional pretreatment prior to use.

(2) In a helium atmosphere and under a pressure of 0.6 kPa, graphite was vaporized in a 1-mm electric arc struck between two d.c.-operated graphite electrodes in a vacuum apparatus. The product deposited on the cathode was removed as described in section (1), was ground and then converted into ruthenium catalyst.

1b. Hydrogenation of Carbon Monoxide

The heterogeneous hydrogenation of carbon monoxide was carried out in a fixed-bed continuous reactor under atmospheric pressure and at a temperature in the range from 200 to 300° C. As contact catalyst, use was made of a 2 cm-high pouring comprising 100 mg of catalyst obtained according to 1a.(1) and the same amount of inert glass beads. The repurified educt gases were used in a $H_2$:CO ratio of 3:1 at a total flow rate of 20 ml/min. The product gases were determined by means of a gas chromatograph coupled to the synthesizing apparatus.

Figure 2:
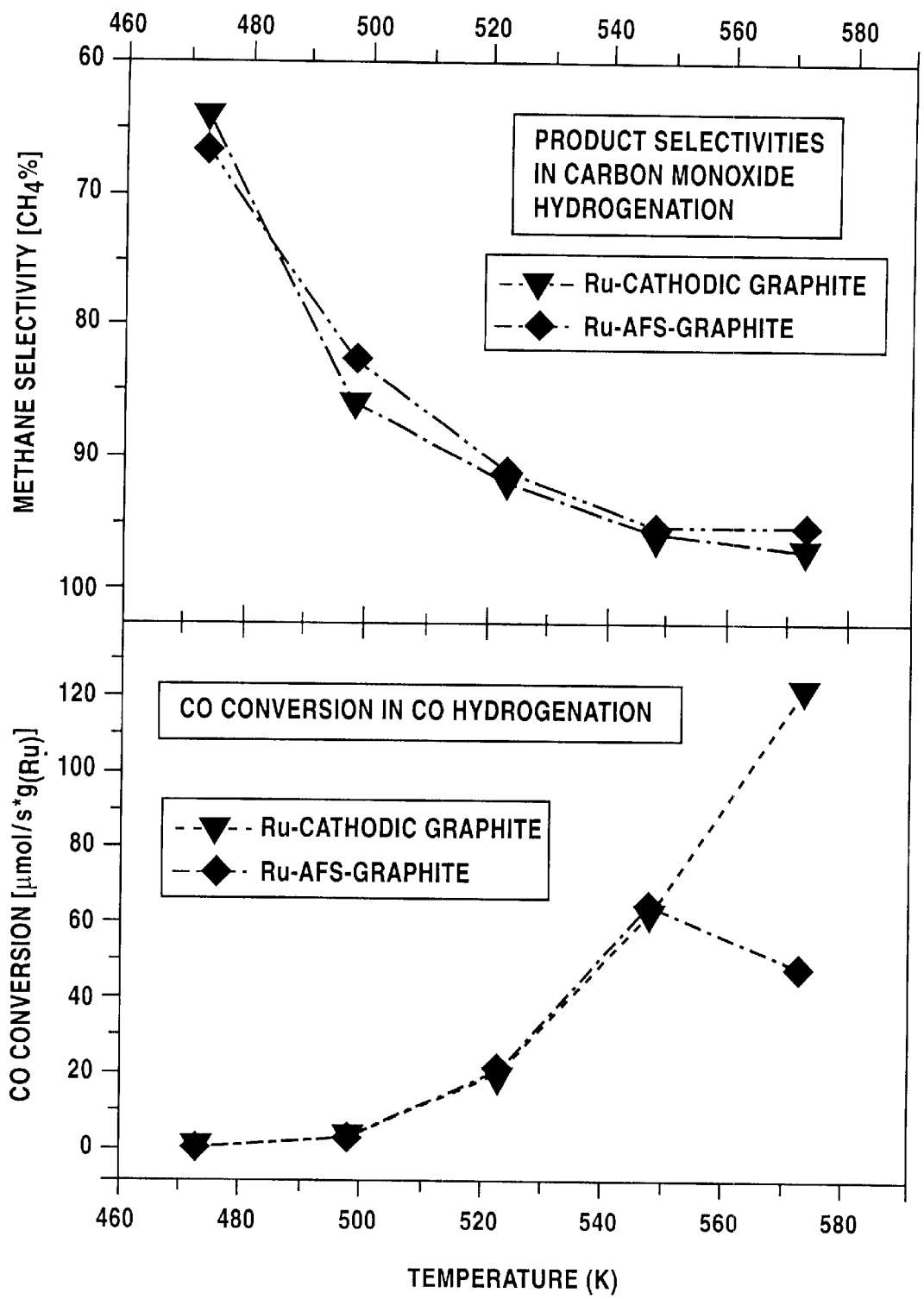
FIG. 2 shows, in analogy to FIG. 1, a comparison of the catalytic activities and the product selectivities of ruthenium deposited on the cathode carbon deposit, as described in the invention, and Ru-AFS-graphite It is apparent from this graph that the catalyst containing cathodic-deposited carbon and ruthenium bound thereto, while showing almost identical product selectivity to that of the graphitic reference system, shows significantly higher catalytic activity at high temperatures. The drop in the catalytic activity of the graphitic system was found to be due to agglomeration of the metal particles, which caused a reduction in the surface area of the catalytically active metal.

The procedure was repeated under the same conditions using ruthenium catalysts bound to graphite. The results are recorded in the FIGS. 1 and 2.

2a. Production of an Amorphous Carbon Catalyst

Graphite was vaporized at 400 mbar under helium atmosphere in an electric arc generated by d.c. and the product was stripped off the water-cooled walls of the apparatus after the arc was turned off. Soluble fullerenes were stripped off the amorphous carbon by extraction with refluxing toluene in a Soxhlet apparatus, subsequently removing any solvent adhering to the residue in vacuo. The amorphous carbon catalyst is termed catalyst TB74.

2b. Partial Oxidation of Methanol

Figure 3:
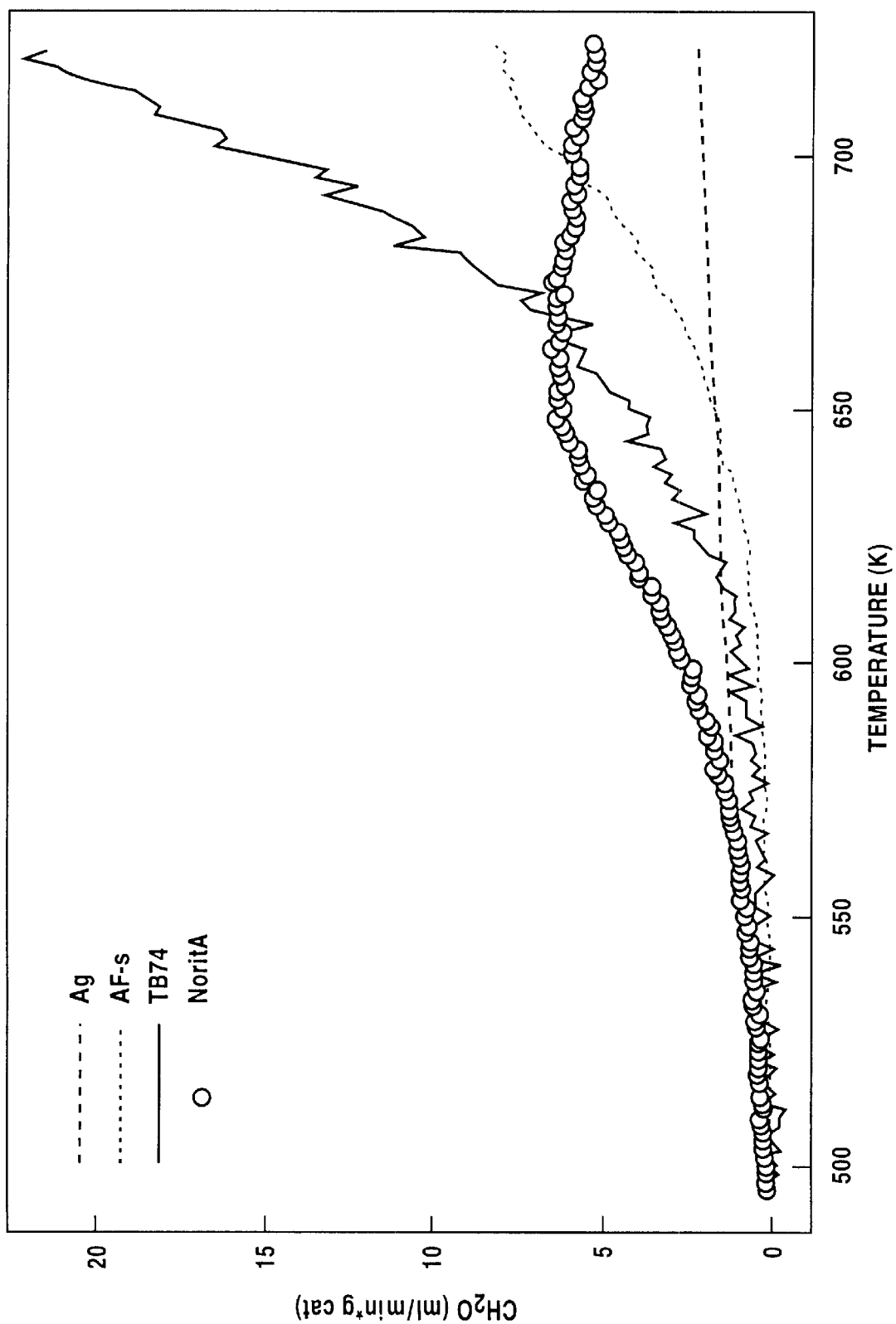
FIG. 3 shows that a catalyst according to the invention without a catalytically active metal, i.e., a catalyst which consists only of the amorphous carbon in accordance with the invention (TB 74) exhibits a much higher mass yield compared to natural graphite (AF-S), activated carbon (Norit A) and a technical silver catalyst (Ag) between about 670 and 720° K. This yield is obtained at a temperature which basically lies below the value commonly used in industrial practice, which contributes considerably to energy saving.

The heterogeneously catalyzed oxidation of methanol to formaldehyde was carried out in a solid bed reactor at a temperature range of 200 to 450° C. The educt gases $CH_3OH$ and $O_2$ were applied at a ratio of 3:1 at a constant space velocity of 11 700 $h^{-1}$. The product gases were determined via ion molecule reaction-mass spectrometry (IMR-MS). The results are recorded in FIG. 3.

We claim:

1. A method for the liquid-phase hydrogenation of organic molecules, the method comprising contacting a solvent solution containing the organic molecules and hydrogen in the presence of a catalyst under hydrogenation conditions, wherein said catalyst consists of amorphous carbon with molecular planes that have curved surfaces and contain six-membered and non-six-membered carbon rings and wherein the solvent is at least one member selected from the group consisting of tetrahydrofuran, dichloromethane and toluene.

2. The method of claim 1, wherein the organic molecule is an olefin.

3. The method of claim 1, wherein the organic molecule is a ketone.

4. The method of claim 1, wherein the organic molecule is an aromatic nitro compound.

* * * * *